United States Patent [19]
Barrow et al.

[11] Patent Number: 5,846,570
[45] Date of Patent: Dec. 8, 1998

[54] STABILIZED HYDROGEN PEROXIDE GEL COMPOSITIONS

[75] Inventors: Stephen Roy Barrow, Trumbull; Jesus Antonio Urbaez, Waterbury, both of Conn.

[73] Assignee: Chesebrough-Pond's USA Co., Division of Conopco, Inc., Greenwich, Conn.

[21] Appl. No.: 884,047

[22] Filed: Jun. 27, 1997

[51] Int. Cl.⁶ .................................................. A61K 33/40
[52] U.S. Cl. ............................... 424/616; 424/53; 424/57; 514/970; 514/973
[58] Field of Search ......................... 424/616, 53

[56] References Cited

U.S. PATENT DOCUMENTS

| | | |
|---|---|---|
| 4,226,851 | 10/1980 | Sompayrac . |
| 4,788,052 | 11/1988 | Ng et al. . |
| 4,839,156 | 6/1989 | Ng et al. . |
| 4,839,157 | 6/1989 | Ng et al. . |
| 5,059,417 | 10/1991 | Williams et al. . |
| 5,180,517 | 1/1993 | Woods . |
| 5,217,710 | 6/1993 | Williams et al. . |
| 5,326,494 | 7/1994 | Woods . |

*Primary Examiner*—Leonard Schenkman
*Attorney, Agent, or Firm*—Milton L. Honig

[57] ABSTRACT

An oral composition, particularly a gel, is provided which includes at least 2%, preferably 6% or higher of hydrogen peroxide in a carrier stabilized by a triphenylmethane dye. Particularly useful as the dye are FD&C Blue 1 and FD&C Green 3 at levels ranging from 0.006 to 1 %. Further stability can also be achieved through use of a chelating acid, particularly phosphoric acid.

7 Claims, No Drawings

STABILIZED HYDROGEN PEROXIDE GEL COMPOSITIONS

BACKGROUND OF THE INVENTION

1. Field of the Invention

The invention relates to peroxide containing gel dentifrices stabilized against decomposition.

2. The Related Art

Aqueous hydrogen peroxide is widely viewed by the dental profession as an effective treatment against gum disease. Periodontal disorders are believed to arise from infectious anaerobic microorganisms which are active in the absence of oxygen. These microorganisms can be controlled or entirely eliminated by contact with peroxides which release oxygen. According to this rationale, oxygen creates an aerobic atmosphere destructive to the microorganisms.

Facile reactivity of the peroxide benefits performance but conversely results in storage stability problems. Dentifrices containing peroxides tend to decompose within a relatively short period of time. Not only is activity lost but there can be a marked breakdown in the dentifrice's physical properties. Dentifrice viscosity is particularly adversely affected by the chemical breakdown of thickening agents. A variety of techniques have been developed to counter the problem.

U.S. Pat. No. 4,226,851 (Sompayrac) discloses oral compositions comprising hydrogen peroxide and zinc chloride wherein vitamin E is added as a stabilizing agent. U.S. Pat. No. 4,788,052 and U.S. Pat. No. 4,839,157 both to Ng et al. report aqueous hydrogen peroxide gel dentifrices stabilized with a combination of hydrophilic and hydrophobic fumed silica. These gels include polyethylene glycol, sodium saccharin, sodium benzoate, polyethylene oxide type nonionic surfactant and flavor all maintained at a pH of 3–6, preferably 4.5–5, through acidification with phosphoric or citric acids. A related patent, U.S. Pat. No. 4,839,156 (Ng et al.), further specifies use of polyoxyethylene-polyoxypropylene block copolymers, polyethylene glycol, nonionic surfactant and flavor. Again citric or phosphoric acids maintain a pH of about 4.5 to 6.

U.S. Pat. No. 5,059,417 (Williams et al.) reports on clear gel dentifrices having a criticality in this ratio of glycerol to polyoxyethylene-polyoxypropylene copolymer. Phosphoric acid is indicated to be beneficial as an acidifying agent.

Tin compounds are described in U.S. Pat. 5,217,710 (Williams et al.) as stabilizing fluoride induced gel decomposition.

U.S. Pat. No. 5,326,494 and U.S. Pat. No. 5,180,517, both to Woods, describe arylazo compounds, such as tartrazine, for stabilizing sodium perborate containing cleaning liquids.

Many of these advances have proved useful for relatively dilute hydrogen peroxide systems. Higher levels require further measures. There remains a need to discover improved systems. Consequently, systems have been sought for use in oral compositions that impart to the consumer satisfactory taste, contribute no disruptive influence upon rheology, and maintain active peroxide levels even under stressing temperature conditions.

Accordingly, it is an object of the present invention to provide a relatively concentrated hydrogen peroxide containing oral composition that is peroxide stable even at elevated temperatures over extended periods of time.

Another object of the present invention is to provide a relatively highly concentrated hydrogen peroxide gel dentifrice which maintains viscosity even after extended storage.

These and other objects of the present invention will become more readily apparent upon consideration of the summary, detailed descriptions and examples which follow.

SUMMARY OF THE INVENTION

An oral composition in semi-solid form is provided which includes:
  (i) from 2 to 15% by weight of hydrogen peroxide;
  (ii) from 0.006 to 1% by weight of a triphenyl methane dye; and
  (iii) a pharmaceutically acceptable carrier.

DETAILED DESCRIPTION

Now it has been found that gel compositions containing at least 2% hydrogen peroxide can be stabilized with a triphenylmethane dye, particularly with FD&C Blue 1 or Green 3. Stabilization can also be enhanced through a chelating acid.

Accordingly, compositions of the present invention will require a triphenylmethane dye for stabilization of the peroxide. Particularly suitable are dyes having the structure:

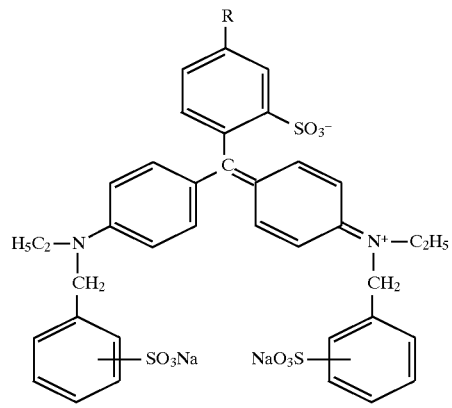

wherein R is a hydrogen, hydroxyl, carboxyl or acyloxy radical. Most preferred is when R is either hydrogen representing FD&C Blue 1 or hydroxy representing FD&C Green 3. Amounts of the dye will range from 0.006 to 1%, preferably from 0.01 to 0.1% by weight.

Another essential element of the claimed invention is hydrogen peroxide. Amounts of the peroxide may range from 2 to 15%, preferably from 3 to 8%, optimally from 5 to 10% by weight.

Chelating acids may also be present to stabilize against peroxide decomposition. Typical chelating acids include citric acid, lactic acid, malic acid, fumaric acid, tartaric acid, phosphoric acid and mixtures thereof. Most preferred is phosphoric acid. Amounts of the chelating acid may range from 0.16 to 5%, preferably from 0.2 to 2%, optimally from 0.25 to 0.8% by weight. The semi-solid compositions of the present invention may either be in paste or gel form. Most preferably it is in gel form.

A further essential component of the present invention is that of a pharmaceutically acceptable semi-solid carrier. The carrier may include such functional ingredients as water, humectants, abrasives, thickeners and surfactants. Total levels of these materials may range anywhere from 0.1 to 99.9%, preferably from 20 to 99% by weight.

Oral compositions of the present invention may further include, besides a peroxide composition, an additional separate bicarbonate-containing composition, each composition being held within a separate container available for simultaneous delivery in substantially equal volumes for use in the mouth.

The bicarbonate compositions may also contain a fluoride anticaries compound. Especially preferred is sodium fluoride. Bicarbonate salts will usually be present in alkali metal form, examples of which are sodium and potassium. Typically, the concentration of bicarbonate salt will range from 0.5 to 80%, preferably from 2 to 50%, optimally between 5 and 20% by weight of the total combined dental product. The pH of the bicarbonate composition may range from 7.0 to 9.5, most preferably 8.0 to 9.0. Typically the bicarbonate composition will include a natural or synthetic thickening agent in an amount about 0.1 to 10%, preferably 0.5 to 5% by weight. Thickeners can be selected from hydroxypropyl methyl cellulose, hydroxyethyl cellulose, sodium carboxymethyl cellulose, xanthan gum, tragacanth gum, karaya gum, arabic gum, Irish moss, starch, alginates and carrageenans.

Water may be present in the compositions in amounts ranging from about 20 to about 99% by weight. When the peroxide composition is a gel, the amount of water may range from about 30 to about 55%, optimally between 35 and 45% by weight.

Humectants are usually polyols which, for example, may include glycerol, sorbitol, propylene glycol, lactitol, xylitol, polypropylene glycol, polyethylene glycol, hydrogenated corn syrup and mixtures thereof. Generally the amount of humectant will range from 25 to 90%, preferably from 40 to 70% by weight.

When the peroxide compositions are in the form of a gel, it may be desirable to utilize a thickening agent that is a combination of water and a crosslinked acrylic polymer and/or a polyoxyethylene/polyoxypropylene copolymer. Most preferred is the polyoxyethylene/polyoxypropylene copolymer, especially one having a hydrophobic portion, represented by ($C_3H6O$), with a molecular weight range from about 2,750 to 4,000 and a hydrophilic portion, represented by ($C_2H_4O$), constituting about 70–80% of the weight of the copolymer.

Commercially, the above mentioned copolymers are available from the BASF Corporation under the trademark, Pluronic F88, F99, F108 and F127. Most preferred is Pluronic F127 (more commonly described by its CTFA name, Poloxamer 407) which has a molecular weight ranging from about 10,000 to 15,000, and containing about 70% of the hydrophilic polyoxyethylene moiety. Amounts of the copolymer can range anywhere from 18–25% by weight, preferably between 19 and 24%. Polyoxamers are particularly suitable for this invention because of their wide pH tolerance, high compatibility with hydrogen peroxide and unique gel properties.

The carrier may include an abrasive. Illustrative abrasives are, silicas, aluminas, calcium carbonate and salts of metaphosphate. Especially preferred are alumina and silica. Amounts of the abrasive may range from 5 to 80% by weight.

Surfactants may also be a constituent of the pharmaceutically acceptable carrier. The surfactant may be of the anionic, nonionic, cationic or amphoteric type. Most preferred are sodium lauryl sulphate, sodium dodecylbenzene sulphonate and sodium laurylsarcosinate. Surfactants are usually present in amounts from 0.5 to 10%, preferably from 1 to 5% by weight.

Tartar control agents may be incorporated into compositions of this invention, especially effective will be zinc salts (e.g. zinc citrate trihydrate) and agents containing phosphorous. Inorganic phosphorous tartar control agents may include any of the pyrophosphates such as disodium pyrophosphate, dipotassium pyrophosphate, tetrapotassium pyrophosphate, tetrasodium pyrophosphate and mixtures thereof. Organic phosphorous compounds that may serve as tartar control agents include polyphosphonates such as disodium ethane-1-hydroxy-1, 1-diphosphonate (EHDP), methanediphosphonic acid, and 2-phosphonobutane-1 ,2,4-tricarboxylic acid.

For anti-caries protection, a source of fluoride ion may be present. Fluoride sources include sodium fluoride, potassium fluoride, calcium fluoride, stannous fluoride, stannous monofluorophosphate and sodium monofluorophosphate. These sources should release anywhere from 25 to 3500 ppm of fluoride ion. The anti-caries agent may be present in an amount from 0.05 to 3%, preferably 0.2 to 1% by weight of the composition.

Sweetening agents such as saccharin, sodium cyclamate, aspartame, sucrose and the like may be included at levels from 0.1 to 5% by weight.

Other additives may also be incorporated into the oral compositions including preservatives, silicones, other synthetic or natural polymers such as Gantrez S-97, and anti-gingivitis actives.

The following examples will more fully illustrate the embodiments of this invention. All parts, percentages and proportions referred to herein and in the appended claims are by weight of the total composition unless otherwise stated.

EXAMPLE 1

Typical of the present invention is a peroxide gel composition whose formulation is detailed under Table I. The formulation of Table I may be utilized either separately or in combination with a bicarbonate composition detailed under Table II, each of the compositions being held in a separate compartment of a dual compartment dispenser.

TABLE I

Peroxide Gel Component

| INGREDIENT | WEIGHT % |
|---|---|
| Pluronic F127 | 20.0 |
| Glycerin | 40.0 |
| Hydrogen Peroxide (35% food grade) | 17.00 |
| Methyl Salicylate | 0.50 |
| FD&C Blue 1 | 0.01 |
| Phosphoric Acid 95% W/W | 0.30 |
| Deionized Water | Balance |

TABLE II

Bicarbonate Paste Component

| INGREDIENT | WEIGHT % |
|---|---|
| Polyol II (sorbitol and other sugars) | 48.71 |
| Syloid 63XX (abrasive silica) | 15.00 |
| Sodium Bicarbonate | 10.00 |
| PEG 32 (polyethylene glycol) | 5.00 |
| Sylox 15x (thickening silica) | 6.00 |
| Sodium Lauryl Sulfate | 2.98 |
| SD Alcohol 38B | 2.85 |
| Cellulose Gum | 0.80 |
| Menthol | 0.50 |
| Sodium Saccharin | 0.50 |
| Sodium Fluoride | 0.44 |
| Titanium Dioxide | 0.23 |
| Deionized Water | Balance |

EXAMPLE 2

A series of stability experiments were conducted to evaluate the effect of FD&C Blue 1 (and FD&C Green 3) and phosphoric acid concentrations on a peroxide gel composition.

The test employed was the Peroxide Stability/Stress Test (PSST). Samples were exposed to accelerated aging at a temperature of 95° C. over a 6 hour period. These aging conditions were found to have good correlation with 3 month storage stability testing at 105° F. Peroxide content of the gel was assayed by oxidizing potassium iodide to iodine and titrating with sodium thiosulphate on an auto-titrator fitted with redox electrode.

Gel compositions having the same ingredients (except for different dye and phosphoric acid concentrations) as that identified under Table I of Example 1 were herein evaluated. Set A compositions were processed under ultra clean conditions. Set B compositions were processed under production type conditions in stainless steel mixers. Table III outlines the results of these tests.

TABLE III

Peroxide Stability Results*

| PROCESS CONDITIONS SET | PEROXIDE CONCENTRATION (WEIGHT %) | CONTROL (0.005% DYE AND 0.15% PHOSPHORIC ACID) PERCENT RECOVERY | SAMPLE 1 (0.01% DYE AND 0.30% PHOSPHORIC ACID) PERCENT RECOVERY | SAMPLE 2 (0.005% DYE AND 0.30% PHOSPHORIC ACID) PERCENT RECOVERY | SAMPLE 3 (0.01% DYE AND 0.15% PHOSPHORIC ACID) PERCENT RECOVERY |
|---|---|---|---|---|---|
| A | 4.0 | 79 | 94 | 95 | 90 |
| A | 6.0 | 83 | 93 | 94 | 91 |
| B | 3.0 (batch mixer not fully passivated) | — | 97 | 92 | 88 |
| B | 3.0 (mixer fully passivated) | — | 96 | 94 | 87 |

*FD&C Blue 1 was used as the dye; similar results were obtained with FD&C Green 3.

Evident from Table III is that by increasing the dye and/or phosphoric acid concentrations, enhanced peroxide stability resulted. It is to be noted that percent recovery above 85.0% peroxide correlates with traditional storage at room temperature up to three years. However, it is preferred to have recoveries in the 90.0% or higher range. Gels in the 95.0% or higher range usually have exceptional field stability.

The foregoing description and examples illustrate selected embodiments of the present invention. In light thereof variations and modifications will be suggested to one skilled in the art, all of which are within the spirit and purview of this invention.

What is claimed is:

1. An oral semi-solid composition comprising:
    (i) from 2 to 15% by weight of hydrogen peroxide;
    (ii) from 0.01 to 1% by weight of a triphenyl methane dye selected from the group consisting essentially of FD&C Blue 1 and FD&C Green 3;
    (iii) from 0.15 to 5% by weight of phosphoric acid; and
    (iv) a pharmaceutically acceptable carrier.

2. The composition according to claim 1 wherein the hydrogen peroxide is present in an amount from 3 to 8% by weight.

3. The composition according to claim 1 wherein the dye is present from 0.01 to 0.1% by weight.

4. The composition according to claim 1 wherein the carrier comprises a humectant selected from the group consisting of polyoxyethylene-polyoxypropylene copolymer, glycerol, sorbitol and mixtures thereof.

5. The composition according to claim 1 wherein the phosphoric acid is present in an amount from 0.25 to 0.8% by weight.

6. The composition according to claim 1 in the form of a gel.

7. An oral semi-solid composition comprising:
    (i) from 2 to 15% by weight of hydrogen peroxide;
    (ii) from 0.005 to 1% of a triphenyl methane dye selected from the group consisting essentially of FD&C Blue 1 and FD&C Green 3;
    (iii) from 0.3 to 5% by weight of phosphoric acid; and
    (iv) a pharmaceutically acceptable carrier.

* * * * *